(12) United States Patent
Ichijo et al.

(10) Patent No.: US 10,723,674 B2
(45) Date of Patent: Jul. 28, 2020

(54) UNSATURATED HYDROCARBON PRODUCTION METHOD AND CONJUGATED DIENE PRODUCTION METHOD

(71) Applicant: JXTG NIPPON OIL & ENERGY CORPORATION, Tokyo (JP)

(72) Inventors: Tatsuya Ichijo, Tokyo (JP); Nobuhiro Kimura, Tokyo (JP)

(73) Assignee: JXTG NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 16/084,856

(22) PCT Filed: Mar. 10, 2017

(86) PCT No.: PCT/JP2017/009777
§ 371 (c)(1),
(2) Date: Sep. 13, 2018

(87) PCT Pub. No.: WO2017/159570
PCT Pub. Date: Sep. 21, 2017

(65) Prior Publication Data
US 2019/0055174 A1 Feb. 21, 2019

(30) Foreign Application Priority Data
Mar. 15, 2016 (JP) .................... 2016-050890

(51) Int. Cl.
| | | |
|---|---|---|
| *C07C 5/333* | (2006.01) |
| *B01J 35/10* | (2006.01) |
| *B01J 35/00* | (2006.01) |
| *B01J 37/03* | (2006.01) |
| *B01J 37/02* | (2006.01) |
| *B01J 23/00* | (2006.01) |
| *B01J 21/04* | (2006.01) |
| *B01J 23/02* | (2006.01) |
| *B01J 23/62* | (2006.01) |

(52) U.S. Cl.
CPC ............ *C07C 5/3337* (2013.01); *B01J 21/04* (2013.01); *B01J 23/005* (2013.01); *B01J 23/02* (2013.01); *B01J 23/626* (2013.01); *B01J 35/0073* (2013.01); *B01J 35/1014* (2013.01); *B01J 35/1038* (2013.01); *B01J 35/1061* (2013.01); *B01J 37/0201* (2013.01); *B01J 37/0203* (2013.01); *B01J 37/0207* (2013.01); *B01J 37/031* (2013.01); *C07C 5/3332* (2013.01); *C07C 2521/04* (2013.01); *C07C 2521/10* (2013.01); *C07C 2523/62* (2013.01)

(58) Field of Classification Search
CPC . C07C 5/3337; C07C 5/3332; C07C 2521/04; C07C 2521/10; C07C 2523/62; B01J 23/02; B01J 23/626; B01J 35/1061; B01J 37/031; B01J 21/04; B01J 23/005; B01J 35/0073; B01J 35/1014; B01J 35/1038; B01J 37/0201; B01J 37/0203; B01J 37/0207
See application file for complete search history.

(56) References Cited

U.S. PATENT DOCUMENTS

| | | | |
|---|---|---|---|
| 2,433,800 A | 12/1947 | Watson | |
| 5,817,596 A | 10/1998 | Akporiaye et al. | |
| 2004/0266612 A1 | 12/2004 | Hayes et al. | |
| 2012/0065443 A1* | 3/2012 | Mabande ................ | B01J 23/42 585/430 |
| 2014/0200379 A1* | 7/2014 | Josch ...................... | C07C 5/48 585/326 |
| 2014/0309470 A1 | 10/2014 | Park et al. | |
| 2015/0038758 A1 | 2/2015 | Park et al. | |
| 2018/0133694 A1 | 5/2018 | Park et al. | |

FOREIGN PATENT DOCUMENTS

| | | | | |
|---|---|---|---|---|
| JP | S27-001758 A | 5/1952 | | |
| JP | S57-140730 A | 8/1982 | | |
| JP | S60-001139 A | 1/1985 | | |
| JP | 10180101 A | * 7/1998 | ........... | C07C 5/3337 |
| JP | H10-180101 A | 7/1998 | | |

(Continued)

OTHER PUBLICATIONS

Kikuchi et al., "Dehydrogenation of n-Butane to Butadiene over Pt—Sn/MgO—Al2O3", Journal of the Japan Petroleum Institute, 55 (1), 2012, pp. 33-39.
International Search Report issued with respect to Application No. PCT/JP2017/009777, dated May 9, 2017 , along with an English translation thereof.
International Preliminary Report on Patentability issued with respect to Application No. PCT/JP2017/009777, dated Sep. 27, 2018, along with an English translation thereof.

*Primary Examiner* — Ali Z Fadhel
(74) *Attorney, Agent, or Firm* — Greenblum & Bernstein, P.L.C.

(57) ABSTRACT

A method for producing a conjugated diene according to an aspect of the present invention comprises a step of contacting a raw material gas containing an alkane with a dehydrogenation catalyst to obtain a product gas containing at least one unsaturated hydrocarbon selected from the group consisting of an olefin and a conjugated diene. In the production method, the dehydrogenation catalyst is a catalyst having a supported metal containing a Group 14 metal element and Pt supported on a support containing Al and a Group 2 metal element; the dehydrogenation catalyst has pores (a) having a pore diameter of 7 nm or more and 32 nm or less; and a proportion of a pore volume of the pores (a) is 65% or more of the total pore volume of the dehydrogenation catalyst.

7 Claims, No Drawings

(56) References Cited

FOREIGN PATENT DOCUMENTS

| | | |
|---|---|---|
| JP | H10-182505 A | 7/1998 |
| JP | 2000-037626 A | 2/2000 |
| JP | 2000-037627 A | 2/2000 |
| JP | 2000-037629 A | 2/2000 |
| JP | 2003-220335 A | 8/2003 |
| JP | 2004-537407 A | 12/2004 |
| JP | 2014-205135 A | 10/2014 |
| JP | 2015-027669 A | 2/2015 |
| WO | 94/029021 A1 | 12/1994 |
| WO | 03/013728 A2 | 2/2003 |
| WO | 2016/152287 A1 | 9/2016 |
| WO | 2016/152796 A1 | 9/2016 |
| WO | 2016/152810 A1 | 9/2016 |

* cited by examiner

UNSATURATED HYDROCARBON PRODUCTION METHOD AND CONJUGATED DIENE PRODUCTION METHOD

TECHNICAL FIELD

The present invention relates to a method for producing an unsaturated hydrocarbon, and a method for producing a conjugated diene.

BACKGROUND ART

An increase in the demand of a conjugated diene including butadiene as a raw material for synthetic rubbers, or the like has been anticipated because of motorization centering on Asia in recent years. For example, a method for subjecting n-butane to a direct dehydrogenation reaction using a dehydrogenation catalyst to produce a conjugated diene (Patent Literature 1) and a method for subjecting n-butene to an oxidative dehydrogenation reaction to produce a conjugated diene (Patent Literatures 2 to 4) have been known as a method for producing a conjugated diene.

CITATION LIST

Patent Literature

Patent Literature 1: Japanese Unexamined Patent Publication No. 2014-205135
Patent Literature 2: Japanese Unexamined Patent Publication No. S57-140730
Patent Literature 3: Japanese Unexamined Patent Publication No. S60-1139
Patent Literature 4: Japanese Unexamined Patent Publication No. 2003-220335

SUMMARY OF INVENTION

Technical Problem

Along with the increase in the demand of unsaturated hydrocarbons, the development of various methods for producing conjugated dienes is required, the method having different features such as demand characteristics, operating cost, and reaction efficiency of a producing device.

An object of the present invention is to provide a method for producing an unsaturated hydrocarbon which can efficiently obtain an unsaturated hydrocarbon from an alkane as a novel production method of an unsaturated hydrocarbon. Another object of the present invention is to provide a method for producing a conjugated diene which can efficiently obtain a conjugated diene for which an increased demand is particularly expected among unsaturated hydrocarbons.

Solution to Problem

The present inventors have found that an alkane can be efficiently converted to an unsaturated hydrocarbon by a catalyst which contains a specific metal element supported on a specific support and has specific pores, and the present invention has thus been completed.

An aspect of the present invention relates to a method for producing an unsaturated hydrocarbon, comprising a step of contacting a raw material gas containing an alkane with a dehydrogenation catalyst to obtain a product gas containing at least one unsaturated hydrocarbon selected from the group consisting of an olefin and a conjugated diene. In the production method, the dehydrogenation catalyst is a catalyst having a supported metal containing a Group 14 metal element and Pt supported on a support containing Al and a Group 2 metal element; the dehydrogenation catalyst has pores (a) having a pore diameter of 7 nm or more and 32 run or less; and a proportion of a pore volume of the pores (a) is 65% or more of the total pore volume of the dehydrogenation catalyst. According to the production method, the unsaturated hydrocarbon can be efficiently obtained from the alkane.

In one aspect, the proportion of the pore volume of the pores (a) may be 70% or more of the total pore volume of the dehydrogenation catalyst. In this case, the above-mentioned effect is more remarkably exhibited.

In one aspect, the Group 14 metal element may be Sn. In this case, the above-mentioned effect is more remarkably exhibited.

In one aspect, the Group 2 metal element may be Mg. In this case, the above-mentioned effect is more remarkably exhibited.

In one aspect, the alkane may be an alkane having 4 to 10 carbon atoms.

In one aspect, the alkane may be butane. At this time, the olefin may be butene, and the conjugated diene may be butadiene. The production method can be particularly suitably employed as a method for producing at least one unsaturated hydrocarbon selected from the group consisting of butene and butadiene.

Another aspect of the present invention relates to a method for producing a conjugated diene, comprising: a first step of contacting a raw material gas containing an alkane with a first dehydrogenation catalyst to obtain a first product gas containing an olefin; and a second step of contacting the first product gas with a second dehydrogenation catalyst to obtain a second product gas containing a conjugated diene. In the production method, the first dehydrogenation catalyst is a catalyst having a supported metal containing a Group 14 metal element and Pt supported on a support containing Al and a Group 2 metal element; the first dehydrogenation catalyst has pores (a) having a pore diameter of 7 nm or more and 32 nM or less; and a proportion of a pore volume of the pores (a) is 65% or more of the total pore volume of the first dehydrogenation catalyst.

Advantageous Effects of Invention

According to the present invention, a method for producing an unsaturated hydrocarbon which can efficiently obtain an unsaturated hydrocarbon from an alkane is provided as a novel production method of an unsaturated hydrocarbon. According to the present invention, a method for producing a conjugated diene which can efficiently obtain a conjugated diene from an alkane is provided.

DESCRIPTION OF EMBODIMENTS

Hereinafter, one suitable embodiment of the present invention will be described. However, the present invention is not limited to the following embodiment at all.

A production method according to the present embodiment comprises a step of contacting a raw material gas containing an alkane with a dehydrogenation catalyst to obtain a product gas containing at least one unsaturated hydrocarbon selected from the group consisting of an olefin and a conjugated diene (hereinafter, referred to as "dehydrogenation step"). In the present embodiment, the dehydrogenation catalyst is a catalyst having a supported metal containing a Group 0.14 metal element and platinum (Pt) supported on a support containing aluminum (Al) and a Group 2 metal element. The dehydrogenation catalyst has pores having a pore diameter of 7 nm or more and 32 nm or less (hereinafter, referred to as "pores (a)"), and a proportion of a pore volume of the pores (a) is 65% or more of the total pore volume of the dehydrogenation catalyst.

By using the dehydrogenation catalyst according to the present embodiment, which contains a specific metal element supported on a specific support and has specific pores, it is possible to react the alkane at a high conversion rate, to obtain the unsaturated hydrocarbon. Since catalyst deterioration is sufficiently suppressed in the production method according to the present embodiment, the replacement or reproduction frequency of the catalyst can be reduced.

Herein, the conversion rate of the alkane, the yield of the olefin, and the yield of the conjugated diene are defined by the following formulae (1), (2), and (3).

$$r_C = \{1 - (m_1/m_0)\} \times 100 \tag{1}$$

$$r_{Y1} = (m_2/m_0) \times 100 \tag{2}$$

$$r_{Y2} = (m_3/m_0) \times 100 \tag{3}$$

$r_C$ in the formula (1) is the conversion rate of the alkane. $m_0$ is the number of moles of the alkane contained in the raw material gas. $m_1$ is the number of moles of the alkane remaining in the product gas.

$r_{Y1}$ in the formula (2) is the yield (%) of the olefin. $m_2$ is the number of moles of the olefin contained in a product gas.

$r_{Y2}$ in the formula (3) is the yield (%) of the conjugated diene. $m_3$ is the number of moles of the conjugated diene contained in the product gas.

In the production method according to the present embodiment, a cause for suppressing deterioration in the dehydrogenation catalyst and a cause for the dehydrogenation catalyst exhibiting excellent dehydrogenation activity are not necessarily clear, but the present inventors speculate as follows.

Since the dehydrogenation catalyst according to the present embodiment contains the Group 2 metal element and the Group 14 metal element, an acid point derived from Al is covered with the Group 2 metal element and the Group 14 metal element. This is considered to cause reduction in acid property of Al, thereby suppressing side reactions such as the cracking reaction of the alkane. It is also considered that the Group 14 metal element and Pt in the dehydrogenation catalyst form bimetallic particles to suppress the aggregation of Pt particles and cause the donation of electrons to Pt from the Group 14 metal element. This is considered to provide improved dehydrogenation activity. Furthermore, it is considered that Pt atoms are diluted in the bimetallic particles, so that the cleavage reaction of a C—C bond caused by the Pt atoms acting on one molecule of the hydrocarbon at multiple points is suppressed. Since, in the dehydrogenation catalyst according to the present embodiment, the proportion of the pore volume of the pores (pores (a)) of the specific pore diameter in the dehydrogenation catalyst is equal to or greater than a specific proportion, it is considered that the dispersibility of the bimetallic particles on the support is high, and the dehydrogenation catalyst exhibits excellent dehydrogenation activity.

In the present embodiment, the raw material gas contains the alkane. The number of carbons of the alkane may be the same as that of the intended unsaturated hydrocarbon. The number of carbons of the alkane may be 4 to 10, or 4 to 6, for example.

The alkane may be, for example, chain-like or cyclic. Examples of the chain-like alkane include butane, pentane, hexane, heptane, octane, and decane. More specific examples of the linear alkane include n-butane, n-pentane, n-hexane, n-heptane, n-octane, and n-decane. Examples of the branched alkane include isobutane, isopentane, 2-methylpentane, 3-methylpentane, 2,3-dimethylpentane, isoheptane, isooctane, and isodecane. Examples of the cyclic alkane include cyclopentane, cyclohexane, cycloheptane, cyclooctane, cyclodecane, and methylcyclohexane. The raw material gas may contain one, or two or more of alkanes.

In the raw material gas, the partial pressure of the alkane may be 1.0 MPa or less, 0.1 MPa or less, or 0.01 MPa or less. By decreasing the partial pressure of the alkane of the raw material gas, the conversion rate of the alkane is likely to be further improved.

The partial pressure of the alkane in the raw material gas is preferably 0.001 MPa or more, and more preferably 0.005 MPa or more from the viewpoint of reducing the size of a reactor with respect to a raw material flow rate.

The raw material gas may further contain an inactive gas such as nitrogen or argon. The raw material gas may further contain steam.

When the raw material gas contains the steam, the content of the steam is preferably 1.0 times moles or more, and more preferably 1.5 times moles or more with respect to the alkane. By incorporating the steam in the raw material gas, deterioration in the activity of the catalyst may be more remarkably suppressed. The content of the steam may be, for example, 50 times moles or less, and is preferably 10 times moles or less with respect to the alkane.

The raw material gas may further contain other ingredients such as hydrogen, oxygen, carbon monoxide, carbon dioxide, olefins, and dienes in addition to the above.

In the present embodiment, the product gas contains at least one unsaturated hydrocarbon selected from the group consisting of an olefin and a conjugated diene. The number of carbons of each of the olefin and the conjugated diene may be the same as that of the alkane, and may be 4 to 10, or 4 to 6, for example.

Examples of the olefin include butene, pentene, hexene, heptene, octene, nonene, and decene. These may be any isomer. Examples of the conjugated diene include butadiene (1,3-butadiene), 1,3-pentadiene, isoprene, 1,3-hexadiene, 1,3-heptadiene, 1,3-octadiene, 1,3-nonadiene, and 1,3-decadiene. The product gas may contain one or two or more of unsaturated hydrocarbons. The product gas may contain an olefin and a conjugated diene.

The production method according to the present embodiment can be particularly suitably used for a method using a raw material gas containing butane as an alkane among the above, that is, a method for producing at least one unsaturated hydrocarbon selected from the group consisting of butene and butadiene. The butane used for producing at least one unsaturated hydrocarbon selected from the group consisting of butene and butadiene may be n-butane or isobutane. The butane may be a mixture of n-butane and isobutane.

Hereinafter, the dehydrogenation catalyst in the present embodiment will be described in detail.

The dehydrogenation catalyst is a solid catalyst catalyzing the dehydrogenation reaction of an alkane. The dehydrogenation catalyst is a catalyst having a supported metal containing a Group 14 metal element and Pt supported on a support containing Al and a Group 2 metal element. Herein, the Group 2 metal element means a metal element belonging to the Group 2 in a long-form element periodic table defined by the International Union of Pure and Applied Chemistry (IUPAC). The Group 14 metal element means a metal element belonging to the Group 14 in a long-form element periodic table defined by the International Union of Pure and Applied Chemistry (IUPAC).

The Group 2 metal element may be at least one selected from the group consisting of beryllium (Be), magnesium (Mg), calcium (Ca), strontium (Sr), and barium (Ba), for example. Among these, when the Group 2 metal element is Mg, the effect of the present invention is more remarkably exhibited.

The Group 14 metal element may be at least one selected from the group consisting of germanium (Ge), tin (Sn), and lead (Pb), for example. Among these, when the Group 14 metal element is Sn, the effect of the present invention is more remarkably exhibited.

In the dehydrogenation catalyst, the content of Al may be 15% by mass or more, or 25% by mass or more based on the total mass of the dehydrogenation catalyst. The content of Al may be 40% by mass or less.

In the dehydrogenation catalyst, the content of the Group 2 metal element is preferably 10% by mass or more, and more preferably 13% by mass or more based on the total mass of the dehydrogenation catalyst. The content of the Group 2 metal element is preferably 20% by mass or less, and more preferably 16% by mass or less based on the total mass of the dehydrogenation catalyst.

In the dehydrogenation catalyst, the content of the Group 14 metal element is preferably 2% by mass or more, and more preferably 4% by mass or more based on the total mass of the dehydrogenation catalyst. The content of the Group 14 metal element is preferably 9% by mass or less, and more preferably 6% by mass or less based on the total mass of the dehydrogenation catalyst.

In the dehydrogenation catalyst, the content of Pt is preferably 0.1% by mass or more, and more preferably 0.5% by mass or more based on the total mass of the dehydrogenation catalyst. The content of Pt is preferably 5% by mass or less, and more preferably 3% by mass or less based on the total mass of the dehydrogenation catalyst. When the content of Pt is 0.1% by mass or more, the amount of platinum per catalyst amount is increased, so that the size of a reactor can be reduced. When the content of Pt is 5% by mass or less, Pt particles formed on the catalyst have a size suitable for the dehydrogenation reaction, to increase the surface area of platinum per unit platinum weight, so that a more efficient reaction system can be achieved.

In the dehydrogenation catalyst, the mole ratio of the Group 14 metal element to Pt (the number of moles of the Group 14 metal element/the number of moles of Pt) is preferably 3 or more, and more preferably 6 or more from the viewpoint of suppressing a side reaction to further improve the producing efficiency of the unsaturated hydrocarbon. The mole ratio of the Group 14 metal element to Pt is preferably 15 or less, and more preferably 13 or less from the viewpoint of preventing the Group 14 metal element from excessively covering the Pt particles to improve the producing efficiency of the unsaturated hydrocarbon.

In the dehydrogenation catalyst, the mole ratio of the Group 2 metal element to Al (the number of moles of the Group 2 metal element/the number of moles of Al) is preferably 0.30 or more, and more preferably 0.40 or more from the viewpoint of suppressing a side reaction to further improve the producing efficiency of the unsaturated hydrocarbon. The mole ratio of the Group 2 metal element to Al is preferably 0.60 or less, and more preferably 0.55 or less from the viewpoint of improving the dispersibility of Pt in the dehydrogenation catalyst.

The contents of Al, Group 2 metal element, Group 14 metal element, and Pt in the dehydrogenation catalyst can be analyzed and confirmed by a method shown in the following Examples.

The dehydrogenation catalyst has pores (a) having a pore diameter of 7 nm or more and 32 nm or less. The dehydrogenation catalyst may have pores having a pore diameter of 3 nm or less (hereinafter, referred to as "pores (b)"), may have pores having a pore diameter of more than 3 nm and less than 7 nm (hereinafter, referred to as "pores (c)"), or may have pores having a pore diameter of more than 32 nm (hereinafter, referred to as "pores (d)").

The proportion of the pore volume of the pores (a) in the dehydrogenation catalyst may be 65% or more of the total pore volume of the dehydrogenation catalyst. When the proportion of the pore volume of the pores (a) is equal to or greater than the above-mentioned proportion, a side reaction is sufficiently suppressed, and sufficient dehydrogenation activity is obtained. The proportion of the pore volume of the pores (a) is preferably 70% or more of the total pore volume of the dehydrogenation catalyst, and more preferably 75% or more from the viewpoint of more remarkably exhibiting the effect of the present invention. The proportion of the pore volume of the pores (a) may be 90% or less of the total pore volume of the dehydrogenation catalyst. The proportion of the pore volume of predetermined pores is measured with a measuring method shown in the following Examples.

The proportion of the pore volume of the pores (b) is preferably 10% or less of the total pore volume of the dehydrogenation catalyst, and more preferably 5% or less. The proportion of the pore volume of the pores (b) may be 1% or more of the total pore volume of the dehydrogenation catalyst.

The proportion of the pore volume of the pores (c) is preferably 15% or less of the total pore volume of the dehydrogenation catalyst, and more preferably 10% or less. The proportion of the pore volume of the pores (c) may be 5% or more of the total pore volume of the dehydrogenation catalyst.

The proportion of the pore volume of the pores (d) is preferably 30% or less of the total pore volume of the dehydrogenation catalyst, and more preferably 20% or less. The proportion of the pore volume of the pores (d) may be 10% or more of the total pore volume of the dehydrogenation catalyst.

The proportion of the sum total pore volume of the pores (a) and the pores (c) is preferably 70% or more of the total pore volume of the dehydrogenation catalyst, and more preferably 80% or more. The proportion of the sum total pore volume of the pores (a) and the pores (c) may be 95% or less of the total pore volume of the dehydrogenation catalyst.

The specific surface area of the dehydrogenation catalyst may be the same as that of a support to be described later.

The support may be a metal oxide support containing Al and a Group 2 metal element, for example. The metal oxide support may be a support containing alumina ($Al_2O_3$) and an oxide of a Group 2 metal, for example, or may be a composite oxide of Al and a Group 2 metal. The metal oxide support may be a support containing a composite oxide of Al and a Group 2 metal element and at least one selected from the group consisting of alumina and an oxide of a Group 2 metal element. The composite oxide of Al and a Group 2 metal may be $MgAl_2O_4$, for example.

The content of Al in the support may be 20% by mass or more, or 30% by mass or more based on the total mass of the support. The content of Al in the support may be 70% by mass or less, or 60% by mass or less based on the total mass of the support.

The content of the Group 2 metal element in the support may be 10% by mass or more, or 15% by mass or more based on the total mass of the support. The content of the Group 2 metal element in the support may be 30% by mass or less, or 20% by mass or less based on the total mass of the support.

The content of the composite oxide of Al and a Group 2 metal element in the support may be 60% by mass or more, or 80% by mass or more based on the total mass of the support. The content of the composite oxide of Al and a Group 2 metal element in the support may be 100% by mass or less, or 90% by mass or less based on the total mass of the support.

The content of alumina in the support may be 10% by mass or more, or 30% by mass or more based on the total mass of the support. The content of alumina in the support may be 90% by mass or less, or 80% by mass or less based on the total mass of the support.

The content of the oxide of the Group 2 metal element in the support may be 15% by mass or more, or 25% by mass or more based on the total mass of the support. The content of the oxide of the Group 2 metal element in the support may be 50% by mass or less, or 35% by mass or less based on the total mass of the support.

The support may contain other metal element in addition to Al and the Group 2 metal element. The other metal element may be at least one selected from the group consisting of Li, Na, K, Zn, Fe, In, Se, Sb, Ni, and Ga, for example. The other metal element may be present as an oxide, or may be present as a composite oxide with at least one selected from the group consisting of Al and a Group 2 metal element.

The support may have pores (a), may have pores (b), may have pores (c), or may have pores (d).

The proportion of the pore volume of each of the pores (a), the pores (b), the pores (c), and the pores (d) in the support may be comparable to that in the above-mentioned dehydrogenation catalyst, for example. Thereby, the dehydrogenation catalyst having a pore volume proportion in the above-mentioned suitable range is likely to be obtained.

The acidity of the support is preferably near neutrality from the viewpoint of suppressing a side reaction. Herein, the acidity of the support is generally evaluated by a pH in a state where the support is dispersed in water. That is, herein, the acidity of the support can be represented by the pH of a suspension in which 1% by mass of the support is suspended. The acidity of the support preferably has a pH of 5.0 to 9.0, and more preferably a pH of 6.0 to 8.0 from the viewpoint of suppressing a side reaction.

The specific surface area of the support may be, for example, 50 $m^2/g$ or more, and is preferably 80 $m^2/g$ or more. Thereby, an effect of being likely to improve the dispersibility of Pt to be supported is exhibited. The specific surface area of the support may be, for example, 300 $m^2/g$ or less, and is preferably 200 $m^2/g$ or less. The support having such a specific surface area tends to have no micropores easily crushed when the support is fired at high temperatures. Thereby, the dispersibility of Pt to be supported tends to be likely to be improved. The specific surface area of the support is measured with a BET specific surface area meter using a nitrogen adsorption method.

A method for preparing the support is not particularly limited, and may be a sol gel method, a coprecipitation method, a hydrothermal synthesis method, an impregnating method, and a solid phase synthetic method or the like, for example. From the viewpoint of easily setting the proportion of the pore volume of the pores (a) to the above-mentioned suitable proportion, the impregnating method is preferable.

As an example of the method for preparing the support, one aspect of the impregnating method will be described below. First, into a solution in which a precursor of a first metal element (for example, a Group 2 metal element) is dissolved in a solvent, a support precursor containing a second metal element (for example, Al) is added, and the solution is stirred. The solvent is then removed under reduced pressure to obtain a solid, and the solid is dried. By firing the dried solid, the support containing the first metal element and the second metal element is obtained. In this aspect, the content of the intended metal element contained in the support can be adjusted by the concentration of the intended metal element in the solution containing the metal element, and the amount of the solution to be used or the like.

The precursor of the metal may be a salt or complex containing the metal element, for example. The salt containing the metal element may be an inorganic salt, an organic acid salt, or hydrates thereof, for example. The inorganic salt may be a sulfate, a nitrate, a chloride, a phosphate, a carbonate, or the like, for example. The organic salt may be an acetate, an oxalate, or the like, for example. The complex containing the metal element may be an alkoxide complex, an amine complex, or the like, for example.

Examples of the solvent dissolving the metal precursor include hydrochloric acid, nitric acid, ammonia water, ethanol, chloroform, or acetone.

Examples of the support precursor containing the second metal element include alumina (for example, γ-alumina). The support precursor can be prepared by a sol gel method, a coprecipitation method, and a hydrothermal synthesis method or the like, for example. Commercially available alumina may be used as the support precursor.

The support precursor may have the pores (a). The proportion of the pore volume of the pores (a) in the support precursor may be 50% or more of the total pore volume of the support precursor, may be 60% or more, or may be 70% or more. In this case, it is easy to set the proportion of the pore volume of the pores (a) in the dehydrogenation catalyst to the above-mentioned suitable proportion. The proportion of the pore volume of the pores (a) may be 90% or less. The proportion of the pore volume of the predetermined pores in the support precursor is measured in the same manner as in the proportion of the pore volume of the predetermined pore diameter in the dehydrogenation catalyst.

Firing can be performed under air atmosphere or oxygen environment, for example. Firing may be performed at one stage, or multi stages of two stages or more. A firing temperature may be a temperature at which a metal precursor can be decomposed, and may be 200 to 1000° C., or 400 to 800° C., for example. When firing is performed at multi stages, at least one stage thereof may be performed at the firing temperature. A firing temperature at other stage may be within the same range as the above, for example, and may be 100 to 200° C.

As conditions during stirring, for example, a stirring temperature can be set to 0 to 60° C., and a stirring time can be set to 10 minutes to 24 hours. As conditions during drying, for example, a drying temperature can be set to 100 to 250° C., and a drying time can be set to 3 hours to 24 hours.

The supported metal containing the Group 14 metal element and Pt is supported on the dehydrogenation catalyst. The supported metal may be supported as an oxide on the support, or may be supported as a metal simple substance on the support.

Other metal element other than the Group 14 metal element and Pt may be supported on the support. Examples of the other metal element are the same as examples of the other metal element which may be contained in the support. The other metal element may be supported as a metal simple substance on the support, may be supported as an oxide, or may be supported as a composite oxide with at least one selected from the group consisting of a Group 14 metal element and Pt.

The amount of the Group 14 metal element supported on the support is preferably 1.5 part by mass or more, and more preferably 3 parts by mass or more with respect to 100 parts by mass of the support. The amount of the Group 14 metal element supported on the support may be 10 parts by mass or less, or 8 parts by mass or less with respect to 100 parts by mass of the support. When the amount of the Group 14 metal element is within the range, catalyst deterioration is further suppressed, so that high activity tends to be maintained over a longer period of time.

The amount of Pt supported on the support is preferably 0.1 parts by mass or more, and more preferably 0.5 parts by mass or more with respect to 100 parts by mass of the support. The amount of Pt supported on the support may be 5 parts by mass or less, or 3 parts by mass or less with respect to 100 parts by mass of the support. In such ranges of an amount of Pt, Pt particles formed on the catalyst have a size suitable for the dehydrogenation reaction, to increase the surface area of platinum per unit platinum weight, so that a more efficient reaction system can be achieved. When such an amount of Pt is in the ranges, high activity can be maintained over a longer period of time while catalyst cost is suppressed.

Examples of a method for supporting the metal on the support include, but not particularly limited to, an impregnation method, a precipitation method, a coprecipitation method, a kneading method, an ionic exchange method, and a pore-filling method.

One aspect of the method for supporting the metal on the support will be shown below. First, a support is added into a solution in which a precursor of an intended metal (supported metal) is dissolved in a solvent (for example, alcohol), and the solution is then stirred. Then, the solvent is removed under reduced pressure to obtain a solid, and the solid is dried. By firing the dried solid, the intended metal can be supported on the support.

In the supporting method, the precursor of the supported metal may be a salt or complex containing the metal element, for example. The salt containing the metal element may be an inorganic salt, an organic acid salt, or hydrates thereof, for example. The inorganic salt may be a sulfate, a nitrate, a chloride, a phosphate, a carbonate, or the like, for example. The organic salt may be an acetate, an oxalate, or the like, for example. The complex containing the metal element may be an alkoxide complex, an ammine complex, or the like, for example.

As conditions during stirring, for example, a stirring temperature can be set to 0 to 60° C., and a stirring time can be set to 10 minutes to 24 hours. As conditions during drying, for example, a drying temperature can be set to 100 to 250° C., and a drying time can be set to 3 hours to 24 hours.

Firing can be performed under air atmosphere or oxygen environment, for example. Firing may be performed at one stage, or multi stages of two stages or more. A firing temperature may be a temperature at which a precursor of a supported metal can be decomposed, and may be 200 to 1000° C., or 400 to 800° C., for example. When firing is performed at multi stages, at least one stage thereof may be performed at the firing temperature. A firing temperature at other stage may be within the same range as the above, for example, and may be 100 to 200° C.

The degree of dispersion of Pt in the dehydrogenation catalyst may be 10% or more, and preferably 15% or more. By the dehydrogenation catalyst having such a degree of dispersion of Pt, a side reaction is further suppressed, so that high activity tends to be maintained over a longer period of time. The degree of dispersion of Pt represents a value measured by a measuring method described in the following Examples.

In one suitable aspect, the dehydrogenation catalyst may be a catalyst having a Group 14 metal element and Pt supported on a support containing Al and a Group 2 metal element (preferably, a support containing $MgAl_2O_4$).

The dehydrogenation catalyst may be molded by methods such as an extrusion molding method and a tablet compression method.

The dehydrogenation catalyst may contain a molding auxiliary agent in the range not to deteriorate the physical properties and catalytic performance of the catalyst from the viewpoint of improving moldability in a molding step. The molding auxiliary agent may be at least one selected from the group consisting of a thickener, a surfactant, a humectant, a plasticizer, and a binder raw material, for example. The molding step of molding the dehydrogenation catalyst may be performed at a suitable stage during the producing step of the dehydrogenation catalyst with consideration of the reactivity of the molding auxiliary agent.

The shape of the molded dehydrogenation catalyst is not particularly limited, and can be appropriately selected according to a form for using the catalyst. For example, the shape of the dehydrogenation catalyst may be a shape such as a pellet shape, a granular shape, a honeycomb shape, or a sponge shape.

The dehydrogenation catalyst to be used may be subjected to a reduction treatment as a pretreatment. The reduction treatment can be performed in a state where the dehydrogenation catalyst is held at 40 to 600° C. under reducing gas atmosphere, for example. A holding time may be 0.05 to 24 hours, for example. The reducing gas may be hydrogen and carbon monoxide or the like, for example.

By using the dehydrogenation catalyst subjected to the reduction treatment, the induction period at an initial stage of a dehydrogenation reaction can be shortened. The induction period at the initial stage of the reaction means a period in a state where there are very few active metals that have been reduced and activated, among active metals contained in the catalyst, and the activity of the catalyst is low.

Subsequently, the dehydrogenation step in the present embodiment will be described in detail.

The dehydrogenation step is a step of contacting a raw material gas with a dehydrogenation catalyst to subject an alkane to a dehydrogenation reaction, thereby obtaining a product gas containing an unsaturated hydrocarbon.

The dehydrogenation step may be carried out by using a reactor filled with a dehydrogenation catalyst, for example, and circulating a raw material gas in the reactor. As the reactor, various reactors used for a gas phase reaction using a solid catalyst can be used. Examples of the reactor include a fixed-bed type reactor, a radial flow type reactor, and a tube-type reactor.

The reaction form of the dehydrogenation reaction may be a fixed-bed type, a moving-bed type, or a fluidized-bed type, for example. Among these, a fixed-bed type is preferred from the viewpoint of equipment cost.

From the viewpoint of reaction efficiency, the reaction temperature of the dehydrogenation reaction, i.e., the temperature in the reactor may be 300 to 800° C., 400 to 700° C., or 500 to 650° C. When the reaction temperature is 300° C. or higher, the amount of production of the unsaturated hydrocarbon tends to be further increased. When the reaction temperature is 800° C. or lower, a caulking speed is not excessively high, so that the high activity of the dehydrogenation catalyst tends to be maintained over a longer period of time.

The reaction pressure, i.e., the atmospheric pressure in the reactor may be 0.01 to 1 MPa, 0.05 to 0.8 MPa, or 0.1 to 0.5 MPa. When the reaction pressure is within the range, the dehydrogenation reaction is likely to proceed, so that more excellent reaction efficiency tends to be obtained.

When the dehydrogenation step is performed in a continuous reaction form for continuously supplying the raw material gas, a weight hourly space velocity (hereinafter, referred to as "WHSV") may be 0.1 $h^{-1}$ or more, or 0.5 $h^{-1}$ or more, for example. WHSV may be 20 $h^{-1}$ or less, or 10 $h^{-1}$ or less. Herein, WHSV is a ratio ("F/W") of the supply rate (amount of supply/time) F of the raw material gas to the mass W of the dehydrogenation catalyst. The ratio WHSV of 0.1 $h^{-1}$ or more can further decrease the size of the reactor. The ratio WHSV of 20 $h^{-1}$ or less can further increase the conversion rate of the olefin. The amounts of the raw material gas and catalyst to be used may be appropriately selected in a more preferable range according to reaction conditions and the activity of the catalyst, or the like, and the WHSV is not limited to the range.

In the dehydrogenation step, the reactor may be further filled with a catalyst other than the dehydrogenation catalyst (hereinafter, referred to as "first dehydrogenation catalyst").

For example, in the present embodiment, the subsequent stage of the first dehydrogenation catalyst of the reactor may be further filled with a solid catalyst (hereinafter, referred to as "second dehydrogenation catalyst") catalyzing the dehydrogenation reaction from the olefin to the conjugated diene. Since the first dehydrogenation catalyst is excellent in the reaction activity of the dehydrogenation reaction from the alkane to the olefin, the subsequent stage of the first dehydrogenation catalyst is filled with the second dehydrogenation catalyst to allow the ratio of the conjugated diene in the obtained product gas to be increased.

The production method according to the present embodiment may further include a step (second step) of contacting the product gas (first product gas) containing the olefin obtained in the dehydrogenation step (first step) with a second dehydrogenation catalyst to subject the olefin to a dehydrogenation reaction, thereby obtaining a product gas (second product gas) containing the conjugated diene. According to such a production method, it is possible to obtain the product gas containing a more conjugated diene.

The second dehydrogenation catalyst can be used without particular limitation as long as it is a catalyst for the dehydrogenation reaction of the olefin. For example, as the second dehydrogenation catalyst, a Pt/$Al_2O_3$-based catalyst often used as a catalyst for a simple dehydrogenation reaction, and a Bi—Mo-based catalyst often used as a catalyst for an oxidization dehydrogenation reaction, or the like can be used.

As described above, the production method according to the present embodiment can efficiently produce the unsaturated hydrocarbon from the alkane. Therefore, the production method according to the present embodiment can reduce the frequency of catalyst reproduction. Because of this, the production method according to the present embodiment is very useful when the unsaturated hydrocarbon (particularly, butene and butadiene) is industrially produced.

While the suitable embodiment of the present invention has been described above, the present invention is not limited to the embodiment.

EXAMPLES

Hereinafter, the present invention will be more specifically described with reference to Examples, but the present invention is not limited to Examples.

Catalyst Synthesis Example 1

<Preparation of Support>

As a support precursor, 6.0 g of γ-alumina classified to 0.5 to 1 mm (NEOBEADS GB-13, manufactured by Mizusawa Industrial Chemicals, Ltd., pH of a suspension having a concentration of 1% by mass in water: 7.9) was prepared. The support precursor and a solution in which 15.1 g of $Mg(NO_3)_2 \cdot 6H_2O$ was dissolved in 45 mL of water were mixed. The obtained mixed solution was stirred at 0.015 MPaA at 40° C. for 30 minutes using a rotary evaporator, and then further stirred under ordinary pressure at 40° C. for 30 minutes. Water was then removed under reduced pressure while the mixed solution was stirred. The obtained solid was dried at 130° C. in an oven overnight. Next, the dried solid was fired at two stages (at 550° C. for 3 hours, and at 800° C. for 3 hours) under an air flow to obtain a support A-1 containing $MgAl_2O_4$.

<Preparation of Catalyst>

3.0 g of the support A-1 and an aqueous solution in which 79.6 mg of $H_2PtCl_6 \cdot 2H_2O$ was dissolved in 16 mL of water were mixed. The obtained mixed solution was stirred at 0.015 MPaA at 40° C. for 30 minutes using a rotary evaporator, and then stirred under ordinary pressure at 40° C. for 30 minutes. Water was then removed under reduced pressure while the mixed solution was stirred. The obtained solid was dried at 130° C. in an oven overnight. Next, the dried solid was fired under an air flow at 550° C. for 3 hours. Next, the obtained fired product and a solution in which 0.311 g of $SnCl_2 \cdot 2H_2O$ was dissolved in 20 mL of EtOH were mixed. The obtained mixed solution was stirred under ordinary pressure at 40° C. for 1 hour using a rotary evaporator, and EtOH was then removed under reduced pressure. The obtained solid was dried at 130° C. in an oven overnight. Next, the dried solid was fired under an air flow at 550° C. for 3 hours, and then subjected to hydrogen reduction to obtain a catalyst A-1. The fired solid was subjected to hydrogen reduction while the solid was held at 550° C. for 2 hours under a flow of a mixed gas in which hydrogen and nitrogen were mixed at 1:1 (mole ratio).

Catalyst Synthesis Example 2

<Preparation of Support>

As a support precursor, 6.0 g of γ-alumina having physical properties shown in Example 2 of Table 1 (manufactured by JGC Catalysts and Chemicals Ltd.) was prepared. The saturated water absorption amount of γ-alumina was 0.547 g per 1 g of γ-alumina. A solution in which 3.0 g of $Mg(NO_3)_2 \cdot 6H_2O$ was dissolved in 3.28 mL of water was dropped into the support precursor to support Mg according to a pore-filling method. The obtained solid was dried at 130° C. in an oven for 1 hour. Next, the dried solid was fired at two stages (at 550° C. for 3 hours, and at 800° C. for 3 hours) under an air flow. In the above procedure, dropping of the aqueous solution of $Mg(NO_3)_2 \cdot 6H_2O$ into the obtained fired product, drying, firing at 550° C., and firing at 800° C. were further repeated 4 times to obtain a support A-2 containing $MgAl_2O_4$.

<Preparation of Catalyst>

A catalyst A-2 was obtained in the same manner as in <Preparation of Catalyst> of Catalyst Synthesis Example 1 except that the support A-2 was used as a support.

Catalyst Synthesis Example 3

A catalyst B-1 was obtained in the same manner as in Catalyst Synthesis Example 1 except that A-204-4 (γ-alumina, manufactured by UNION SHOWA K.K.) was used as a support precursor when a support was prepared.

Catalyst Synthesis Example 4

A catalyst B-2 was obtained in the same manner as in Catalyst Synthesis Example 1 except that D-201 (γ-alumina, manufactured by UNION SHOWA K.K.) was used as a support precursor when a support was prepared.

Catalyst Synthesis Example 5

<Preparation of Support>

105.5 g of $Al(NO_3)_3 \cdot 9H_2O$ and 36.1 g of $Mg(NO_3)_2 \cdot 6H_2O$ were added into 1 L of ion exchange water, followed by vigorous stirring. While the aqueous solution was stirred, a solution obtained by diluting concentrated ammonia water two-fold was dropped at a rate of 0.1 mL/s until the pH of the solution was set to 10, and the solution was left for 30 minutes after being stirred for 30 minutes. The precipitate was filtered, and washed with 1.3 L of ion exchange water twice. Then, the obtained precipitate was dried at 130° C. in an oven overnight. Finally, the dried solid was fired at three stages (at 300° C. for 1 hour, at 500° C. for 2 hours, and at 800° C. for 4 hours) under an air flow to obtain a support 13-3.

<Preparation of Catalyst>

3.0 g of a support B-3 and an aqueous solution in which 79.6 mg of $H_2PtCl_6 \cdot 2H_2O$ was dissolved in 16 mL of water were mixed. The obtained mixed solution was stirred at 0.015 MPaA at 40° C. for 30 minutes using a rotary evaporator, and then further stirred under ordinary pressure at 40° C. for 30 minutes. Water was then removed under reduced pressure while the mixed solution was stirred. The obtained solid was dried at 130° C. in an oven overnight. Next, the dried solid was fired at 550° C. for 3 hours under an air flow. Next, the obtained fired product and a solution in which 0.311 g of $SnCl_2 \cdot 2H_2O$ was dissolved in 20 mL of EtOH were mixed. The obtained mixed solution was stirred under ordinary pressure at 40° C. for 1 hour using a rotary evaporator, and EtOH was then removed under reduced pressure. The obtained solid was dried at 130° C. in an oven overnight. Next, the dried solid was fired under an air flow at 550° C. for 3 hours. Then, the fired product was tablet-compressed to 0.5 mm to 1.0 mm, and then subjected to hydrogen reduction to obtain a catalyst B-3. The fired solid was subjected to hydrogen reduction while the solid was held at 550° C. for 2 hours under a flow of a mixed gas in which hydrogen and nitrogen were mixed at 1:1 (mole ratio).

[Analysis of Support Precursor and Catalyst]

<Specific Surface Area and Proportion of Pore Volume>

The specific surface areas of the support precursor and the catalyst, and the proportion of the pore volume of each of pores (a) (pore diameter: 7 nm or more and 32 nm or less), pores (b) (pore diameter: 3 nm or less), pores (c) (pore diameter: more than 3 nm and less than 7 nm), and pores (d) (pore diameter: more than 32 nm) in the support precursor and the catalyst were measured. The results are shown in Table 1.

In the present Examples, the specific surface areas of the support precursor and the catalyst were measured with a BET specific surface area meter using a nitrogen adsorption method. The proportion of the pore volume of each of the pores (a), the pores (b), the pores (c), and the pores (d) in the support precursor and the catalyst was determined by analyzing the results obtained by measurement at a nitrogen relative pressure of 0 to 0.99 by a nitrogen adsorption method according to a BJH method.

<Composition and Degree of Dispersion of Pt>

In the obtained catalyst A-1, the content of Pt was 0.88% by mass based on the total mass of the catalyst; the content of Sn was 4.3% by mass based on the total mass of the catalyst; the content of Mg was 14.6% by mass based on the total mass of the catalyst; and the content of Al was 35.3% by mass based on the total mass of the catalyst. In the catalyst A-1, the degree of dispersion of Pt was 19.3%.

In the obtained catalyst A-2, the content of Pt was 0.87% by mass based on the total mass of the catalyst; the content of Sn was 4.4% by mass based on the total mass of the catalyst; the content of Mg was 14.3% by mass based on the total mass of the catalyst; and the content of Al was 35.1% by mass based on the total mass of the catalyst. In the catalyst A-2, the degree of dispersion of Pt was 20.1%.

In the obtained catalyst B-1, the content of Pt was 0.61% by mass based on the total mass of the catalyst; the content of Sn was 4.1% by mass based on the total mass of the catalyst; the content of Mg was 15.1% by mass based on the total mass of the catalyst; and the content of Al was 32.4% by mass based on the total mass of the catalyst. In the catalyst B-1, the degree of dispersion of Pt was 2.1%.

In the obtained catalyst B-2, the content of Pt was 0.85% by mass based on the total mass of the catalyst; the content of Sn was 4.6% by mass based on the total mass of the catalyst; the content of Mg was 13.6% by mass based on the total mass of the catalyst; and the content of Al was 34.5% by mass based on the total mass of the catalyst. In the catalyst B-2, the degree of dispersion of Pt was 10.8%.

In the obtained catalyst B-3, the content of Pt was 0.89% by mass based on the total mass of the catalyst; the content of Sn was 4.6% by mass based on the total mass of the catalyst; the content of Mg was 13.9% by mass based on the total mass of the catalyst; and the content of Al was 33.1% by mass based on the total mass of the catalyst. In the catalyst B-3, the degree of dispersion of Pt was 16.9%.

In the present Examples, the content of Pt, the content of Sn, the content of Mg, and the content of Al in the catalyst were measured with an inductively-coupled plasma emission spectrophotometer (ICP-AES). The catalyst was liquefied by dilute hydrochloric acid after alkali fusion for measurement. The measurement conditions will be described below.

Device: SPS-3000 type, manufactured by Hitachi High-Tech Science Corporation
High frequency output: 1.2 kw
Plasma gas flow rate: 18 L/min
Auxiliary gas flow rate: 0.4 L/min
Nebulizer gas flow rate: 0.4 L/min In the present Examples, the degree of dispersion of Pt was measured by a method for measuring the degree of dispersion of metal using CO as adsorption species. A device and measurement conditions or the like will be shown below.

Device: device for measuring degree of dispersion of metal R-6011 manufactured by Ohkura Riken Co., LTD.
Gas flow rate: 30 mL/min (helium, hydrogen)
Amount of sample: about 0.1 g (precisely measured to four decimal places)
Pretreatment: A temperature was risen to 400° C. over 1 hour under a hydrogen stream, to perform a reduction treatment at 400° C. for 60 minutes. The gas was then changed from hydrogen to helium, to purge the hydrogen at 400° C. for 30 minutes, and the temperature was then decreased to room temperature under a helium stream. After a detector was stabilized at room temperature, CO pulsing was performed.
Measurement conditions: Carbon monoxide was pulse-injected by 0.0929 cm3 at room temperature (27° C.) under a stream of normal pressure helium gas to measure the amount of adsorption thereof. The adsorption was performed a number of times until the adsorption was saturated (at least 3 times, at most 15 times). The amount of adsorption of CO of each of Examples is shown in Table 1.

Example 1

A tube-type reactor was filled with 0.8 g of a catalyst A-1, and the reaction tube was connected to a fixed-bed circulation type reaction device. Next, while a mixed gas of hydrogen and nitrogen (hydrogen:nitrogen=1:1 (mole ratio)) was circulated at a rate of 100 mL/min, the temperature of the reactor was raised to 550° C., and the reactor was held at the temperature for 10 minutes. Then, a mixed gas (raw material gas) of n-butane, nitrogen, and water was supplied to the reactor, to subject n-butane in the raw material gas to a dehydrogenation reaction. Herein, the mole ratio of n-butane, nitrogen, and water in the raw material gas was adjusted to 1:5:3. The supply rate of the raw material gas to the reactor was adjusted to 48 mL/min. The WHSV was adjusted to 1 h$^{-1}$. The pressure of the raw material gas of the reactor was adjusted to 0 MPaG.

At a point of time when 1 hour elapsed from the start of the reaction, a product material (product gas) of the dehydrogenation reaction was extracted from the tube-type reactor. At a point of time when 7 hours elapsed from the start of the reaction, a product material (product gas) of the dehydrogenation reaction was extracted from the tube-type reactor. At the start of the reaction, the supply of the raw material gas was started. The product gas extracted at each time was analyzed using a gas chromatograph (TCD-GC) provided with a thermal conductivity detector. As a result of analysis, the product gas was confirmed to contain n-butene (1-butene, t-2-butene, and c-2-butene) and 1,3-butadiene. The concentration (unit: % by mass) of n-butane, the concentration (unit: % by mass) of n-butene, and the concentration (unit: % by mass) of 1,3-butadiene in the product gas extracted at each time were quantified based on the gas chromatograph.

From the concentrations of n-butane, n-butene, and 1,3-butadiene in the product gas, a raw material conversion rate (butane conversion rate), the yield of n-butene (butene yield), and the yield of 1,3-butadiene (butadiene yield) at each time were calculated. The results are shown in Table 1. The butane conversion rate is defined by the following formula (4); the butene yield is defined by the following formula (5); and the butadiene yield is defined by the following formula (6).

$$Rc = (1 - M_P/M_0) \times 100 \quad (4)$$

$$R_{Y1} = M_b/M_0 \times 100 \quad (5)$$

$$R_{Y2} = M_c/M_0 \times 100 \quad (6)$$

Rc in the formula (4) is the butane conversion rate. $R_{Y1}$ in the formula (5) is the butene yield. $R_2$ in the formula (6) is the butadiene yield. $M_0$ in the formulae (4) to (6) is the number of moles of n-butane in the raw material gas. $M_P$ in the formula (4) is the number of moles of n-butane in the product gas. $M_b$ in the formula (5) is the number of moles of n-butene (1-butene, t-2-butene, and c-2 butene) in the product gas. $M_c$ in the formula (6) is the number of moles of 1,3-butadiene in the product gas.

Example 2 and Comparative Examples 1 to 3

The dehydrogenation reaction of n-butane and the analysis of a product gas were performed by the same operation as that of Example 1 except that the catalyst A-1 was changed to a catalyst shown in Table 1. The results are shown in Table 1.

TABLE 1

|  |  | Example 1 | Example 2 | Comparative Example 1 | Comparative Example 2 | Comparative Example 3 |
|---|---|---|---|---|---|---|
| Dehydrogenation catalyst | Kind of catalyst | A-1 | A-2 | B-1 | B-2 | B-3 |
|  | Specific surface area (m²/g) | 106 | 83 | 74 | 101 | 94 |
|  | Total pore volume (cm³/g) | 0.296 | 0.471 | 0.199 | 0.246 | 0.276 |
| Proportion of pore volume (%) | Pores (b) | 1 | 0 | 4.5 | 7 | 2 |
|  | Pores (c) | 15 | 0 | 16.5 | 22.3 | 17 |
|  | Pores (a) | 80 | 86 | 59 | 43.35 | 64 |
|  | Pores (d) | 4 | 14 | 20 | 27.35 | 17 |
|  | Degree of dispersion of Pt (%) | 19.3 | 20.1 | 2.1 | 10.8 | 16.9 |
|  | Amount of adsorption of CO (μmol/g) | 9.9 | 10.3 | 1.1 | 5.5 | 8.6 |

TABLE 1-continued

|  |  |  | Example 1 | Example 2 | Comparative Example 1 | Comparative Example 2 | Comparative Example 3 |
|---|---|---|---|---|---|---|---|
| Support precursor | Specific surface area (m²/g) | | 187 | 217 | 260 | 331 | — |
|  | Total pore volume (cm³/g) | | 0.511 | 0.706 | 0.391 | 0.435 | — |
|  | Proportion of pore volume (%) | Pores (b) | 1 | 0 | 20 | 29 | — |
|  |  | Pores (c) | 14 | 7 | 31.5 | 23.5 | — |
|  |  | Pores (a) | 81.5 | 91 | 33.5 | 29.5 | — |
|  |  | Pores (d) | 3.5 | 2 | 15 | 18 | — |
| Reaction condition | Temperature (° C.) | | 550 | 550 | 550 | 550 | 550 |
|  | Pressure (MPaG) | | 0 | 0 | 0 | 0 | 0 |
|  | WHSV (h⁻¹) | | 1 | 1 | 1 | 1 | 1 |
|  | n-butane:N₂:H₂O (mole ratio) | | 1:5:3 | 1:5:3 | 1:5:3 | 1:5:3 | 1:5:3 |
| Reaction result | Butane conversion rate (%) | After 1 hour | 66.9 | 67.6 | 7.4 | 48.3 | 57.8 |
|  |  | After 7 hours | 59.0 | 61.5 | 5.2 | 44.6 | 52.4 |
|  | Butene yield (%) | After 1 hour | 53.4 | 54.4 | 4.4 | 38.1 | 46.3 |
|  |  | After 7 hours | 46.9 | 49.6 | 2.8 | 34.1 | 41.7 |
|  | Butadiene yield (%) | After 1 hour | 8.8 | 9.3 | 2.7 | 8.1 | 9.0 |
|  |  | After 7 hours | 9.0 | 9.0 | 2.2 | 8.7 | 8.8 |

The invention claimed is:

1. A method for producing an unsaturated hydrocarbon, comprising contacting a raw material gas containing an alkane with a dehydrogenation catalyst to obtain a product gas containing at least one unsaturated hydrocarbon selected from the group consisting of an olefin and a conjugated diene,
wherein:
the dehydrogenation catalyst is a catalyst having a supported metal containing a Group 14 metal element and Pt supported on a support consisting of:
Al,
a Group 2 metal element, and
optionally, a metal element other than zinc,
the dehydrogenation catalyst has pores (a) having a pore diameter of 7 nm or more and 32 nm or less, and
a proportion of a pore volume of the pores (a) is 65% or more of the total pore volume of the dehydrogenation catalyst.

2. The production method according to claim 1, wherein the proportion of the pore volume of the pores (a) is 70% or more of the total pore volume of the dehydrogenation catalyst.

3. The production method according to claim 1, wherein the Group 14 metal element is Sn.

4. The production method according to claim 1, wherein the Group 2 metal element is Mg.

5. The production method according to claim 1, wherein the alkane is an alkane having 4 to 10 carbon atoms.

6. The production method according to claim 1, wherein the alkane is butane, the olefin is butene, and the conjugated diene is butadiene.

7. A method for producing a conjugated diene, comprising:
contacting a raw material gas containing an alkane with a first dehydrogenation catalyst to obtain a first product gas containing an olefin; and
contacting the first product gas with a second dehydrogenation catalyst to obtain a second product gas containing a conjugated diene,
wherein:
the first dehydrogenation catalyst is a catalyst having a supported metal containing a Group 14 metal element and Pt supported on a support consisting of:
Al,
a Group 2 metal element, and
optionally, a metal element other than zinc,
the first dehydrogenation catalyst has pores (a) having a pore diameter of 7 nm or more and 32 nm or less, and
a proportion of a pore volume of the pores (a) is 65% or more of the total pore volume of the first dehydrogenation catalyst.

* * * * *